United States Patent [19]
Schwarze et al.

[11] Patent Number: 6,080,119
[45] Date of Patent: Jun. 27, 2000

[54] PROCESS AND DEVICE FOR GENERATING SHOCK WAVES FOR MEDICAL USES

[75] Inventors: Werner Schwarze, Kreuzlingen; Walter Uebelacker, Buergeln, both of Switzerland; Axel Voss, Egesdorf, Germany

[73] Assignee: HMT Holding AG, Switzerland

[21] Appl. No.: 09/067,733

[22] Filed: Apr. 28, 1998

[30] Foreign Application Priority Data

May 2, 1997 [DE] Germany ............................ 197 18 512

[51] Int. Cl.[7] .................................................. A61B 17/22
[52] U.S. Cl. .............................. 601/4; 367/147; 606/127; 606/128
[58] Field of Search ........................... 601/4, 2; 367/147; 606/127, 128

[56] References Cited

U.S. PATENT DOCUMENTS

| | | | |
|---|---|---|---|
| 4,715,375 | 12/1987 | Nowacki et al. ....................... | 128/328 |
| 4,715,376 | 12/1987 | Nowacki et al. ....................... | 128/328 |
| 4,809,682 | 3/1989 | Forrssmann et al. ..................... | 128/24 |
| 4,932,954 | 6/1990 | Wondrazek et al. .................... | 606/128 |
| 4,938,781 | 7/1990 | Pimiskern ................................ | 29/825 |
| 4,968,395 | 11/1990 | Pavelle et al. ........................... | 204/130 |
| 5,146,912 | 9/1992 | Eizenhoefer .............................. | 128/24 |
| 5,195,508 | 3/1993 | Muller et al. ............................. | 128/24 |
| 5,423,967 | 6/1995 | Kunimatsu et al. ..................... | 204/242 |
| 5,458,652 | 10/1995 | Uebelacker ................................. | 601/4 |

*Primary Examiner*—Marvin M. Lateef
*Assistant Examiner*—Eleni Mantis Mercader
*Attorney, Agent, or Firm*—Eugene E. Renz, Jr., PC

[57] ABSTRACT

Acoustic shock waves for medical uses are generated by an electrical discharge between two electrodes, which are mounted in a liquid medium. A catalyst is added to the liquid medium in the area of the electrodes; this catalyst partially or completely catalytically converts the gas which forms upon application of the voltage to the electrodes back into its original state or partially or completely prevents the formation of the gas.

12 Claims, 1 Drawing Sheet

PROCESS AND DEVICE FOR GENERATING SHOCK WAVES FOR MEDICAL USES

The invention pertains to a process and to a device for generating shock waves for medical uses according to the introductory clauses of claim 1 and claim 2, respectively.

Focussed acoustic shock waves are being used increasingly in human and veterinary medicine for various purposes. Examples are the destruction of concretions, the treatment of soft-tissue complaints and painful orthopedic diseases such as insertion tendinitis and pseudarthrosis, and the induction of bone growth.

Devices for generating shock waves are known in which an electrical breakdown is generated between two electrodes immersed in a liquid medium. The electrical breakdown leads to the explosive vaporization of the liquid medium, as a result of which shock waves are generated. These shock waves are then focussed and conducted into the human or animal body. Devices of this general type are described in, for example, DE-PS 2,635,635, EP 0,590,177 A1, and WO 96/09,621.

The plasma generated during the electrical breakdown leads to the formation of gas bubbles in the liquid medium which interfere with the formation and propagation of the shock waves. It is therefore stated in WO 96/09,621 that a jacket, which is permeable to shock waves and surrounds the electrodes, is provided with at least one opening, through which the gas forming during the spark discharge can escape from the jacket. The openings must be of sufficient size to allow the gas which has formed to escape effectively, which also leads to an exchange between the spaces inside and outside the jacket, as a result of which the conditioning of the liquid medium in the area of the electrodes is impaired. In addition, the gas which has collected outside the jacket must be carried away and removed in the course of a degassing process.

The invention is based on the task of providing a process and a device by means of which the interfering influence of gas formation is decreased.

This task is accomplished in accordance with the invention by a process with the features of claim 1 and by a device with the features of claim 2.

Advantageous designs and elaborations of the invention are given in the subclaims referring to the main claims.

The essential idea of the invention consists in adding a catalyst which opposes the development and formation of gas bubbles to the liquid medium, at least in the area of the medium surrounding the electrodes. During the production of shock waves, there are two different ways in which gas can be formed. When the high-voltage electrical energy required for the spark discharge is applied to the electrodes, the electrical breakdown does not occur immediately. Instead, there is a latent period during which the electric field required for the breakdown builds up. During this latent period, a weak current is already flowing through the liquid medium, the amount of current being determined by the electrical conductance of the medium. This electric current is already enough to lead to an electrolytic decomposition of the liquid medium and thus to the evolution of gas. The catalyst added to the liquid medium is thus able effectively to suppress this electrolytic gas formation during the latent period or even to prevent it almost completely. Once the breakdown channel between the electrodes has formed, so that an electrical discharge between the electrodes can take place, the high discharge current leads to an explosive vaporization of the liquid medium. The catalyst thus has the purpose of catalytically converting the gas formed during the latent period as a result of the incomplete suppression of electrolytic dissociation and in particular of catalytically converting the gas generated by vaporization during the electrical breakdown as quickly and as completely as possible back into some other liquid substance.

The addition of the catalyst according to the invention thus suppresses gas formation during the latent period and leads to a chemical recombination of the gas which is necessarily formed during the discharge.

The liquid medium usually consists mostly of water, so that the gas which forms consists essentially of oxyhydrogen gas. To convert this oxyhydrogen gas back into water, a hydrogenation catalyst is added to the water. Because the water is not completely free of salt, other gases such as chlorine can also form, which can also be catalyzed, dissolved, or converted into substances which are acoustically noninterfering.

In the following, the invention is explained in greater detail on the basis of the exemplary embodiments illustrated in the drawing:

FIG. 1 consists of a side view of a device designed according to the invention in the form of a schematic diagram; and FIG. 2 consists of a diagram, corresponding to FIG. 1, of a second design of the device.

Electrodes 4 and 5 are mounted inside a sleeve 7. Sleeve 7 is permeable to shock waves, is closed at the top, and is sealed off at the bottom by the base of the device. A liquid medium 6, which consists preferably almost entirely of water, is present inside sleeve 7. Liquid medium 6 contains a catalyst 9.

One of the electrodes, namely, electrode 4, is connected in an electrically conductive manner to an internal conductor 1, whereas the other electrode 5 is connected to an outside conductor 3. Internal conductor 1 is insulated by an insulator 2 with respect to external conductor 3. Sleeve 7 is connected by means of an insulator 8 to the rest of the device (not shown), either detachably by a threaded joint, for example, or in permanent fashion. Internal conductor 1 and external conductor 3 are connected in a suitable manner to the high-voltage power supply of the device.

In the exemplary embodiment according to FIG. 1, catalyst 9 is dissolved in liquid form or suspended in solid form in liquid medium 6 surrounding electrodes 4, 5. Liquid medium 6 with catalyst 9 is completely enclosed in sleeve 7. The device according to claim 1 thus represents a complete unit and can be used and replaced as such.

In the embodiment shown in FIG. 2, catalyst 9 is present in the form of a powder in a supply container 11. At the bottom, supply container 11 has a small opening, through which the powdered catalyst 9 can escape into liquid medium 6. The pressure fluctuations arising during the spark discharge between electrodes 4 and 5 encourage a certain amount of catalyst 9 to escape into liquid medium 6, one portion per discharge.

In the exemplary embodiment of FIG. 2, electrodes 4 and 5 and supply container 11 are held in a larger volume [?—Tr. Ed.] of liquid medium 6. This volume can be a closed volume, so that the device with the liquid volume forms an independent, replaceable unit. The volume containing liquid medium 6 can also be connected to an open circuit, through which the liquid medium is circulated and possibly processed.

Catalysts 9 selected for use are essentially known in themselves and are selected in correspondence with the composition of the liquid medium.

Because liquid medium 6 consists preferably almost entirely of water, hydrogenation catalysts are accordingly used as catalyst 9. They catalytically convert the hydrogen-oxygen mixture (oxyhydrogen gas) formed by electrolytic dissociation of the water back into water.

Platinum and palladium metals are preferred as the most effective hydrogenation catalysts. The catalytic effect of these metals depends on how much hydrogen can be absorbed, that is, in particular on how finely the catalyst is distributed. According to the invention, therefore, platinum powder, platinum on active carbon, platinum sponge, platinum black, and, in a corresponding manner, palladium powder, palladium on active carbon, palladium sponge, and palladium black are preferred. The choice and the amount of catalyst added will be based on the effectiveness of the catalyst, on the form in which it is added, on the influences it exerts on the liquid medium, and on the cost of the catalyst.

For the catalysts with the best catalytic effect, such as in the case of palladium black, it has proven effective to add greater than or equal to 0.1 mg per mL of water. Catalysts which are less effective must be added in correspondingly larger amounts. As a rule, the formation and accumulation of gas can be advantageously reduced by the addition of approximately 0.2–4 mg of catalyst per mL of water.

What is claimed is:

1. In the process for generating shock waves for medical uses by application of a high electrical voltage to two electrodes mounted in a liquid medium, wherein the improvement comprises adding to said liquid medium at least in the area surrounding the electrodes an effective amount of a catalyst to suppress electrolytic formation of gases due to application of said high voltage to said electrodes.

2. In the process for generating shock waves for medical uses by application of a high electrical voltage to two electrodes mounted in a liquid medium, wherein the improvement comprises adding to said liquid medium at least in the area surrounding the electrodes an effective amount of a catalyst to promote formation of said liquid medium by recombination of gases formed by application of said high voltage to said electrodes.

3. A process for suppressing formation and/or promoting recombination of gases formed during generation of shock waves by application of a high electrical voltage to two electrodes mounted in a liquid medium, which process comprises adding to said liquid medium an effective amount of a catalyst to suppress formation and/or promote recombination of said gases.

4. A device for generating shock waves for medical uses by means of a high voltage electrical spark discharge comprising:
   (a) a pair of electrical spark discharge electrodes; and
   (b) a liquid medium containing an effective amount of a catalyst to suppress formation and/or promote recombination of gases formed as a result of said high voltage electrical spark discharge.

5. The device of claim 4 wherein said liquid medium is water and the catalyst is a hydrogenation catalyst.

6. The device of claim 5 wherein said hydrogenation catalyst is selected from the group consisting of platinum and palladium.

7. The device of claim 6 wherein said catalyst is platinum and said platinum catalyst is selected from the group consisting of platinum on active carbon, platinum powder, platinum sponge and platinum black.

8. The device of claim 6, wherein said catalyst is palladium and said palladium catalyst is selected from the group consisting of palladium on active carbon, palladium powder, palladium sponge and palladium black.

9. The device according to claims 4, 5, 6, 7, or 8 wherein the catalyst concentration is at least 0.1 mg/ml.

10. The device according to claim 9, wherein the catalyst concentration is 0.2–4 mg/ml.

11. A device for generating shock waves for medical uses by means of a high voltage electrical spark discharge comprising:
    (a) a pair of electrical spark discharge electrodes;
    (b) a liquid medium; and
    (c) a catalyst dispersed in said liquid medium in an effective amount to suppress formation and/or promote recombination of gases formed as a result of said high voltage electrical spark discharge.

12. A device for producing shockwaves by means of an electrical spark gap discharge comprising: a housing containing a liquid medium; a pair of closely-spaced discharge electrodes, an enclosure disposed about said electrodes in said housing; an electrically conductive liquid medium filling said enclosure, said electrically conductive liquid medium having an effective amount of a catalyst to suppress formation and/or promote recombination of gases formed as a result of said high voltage electrical spark discharge.

* * * * *

(12) EX PARTE REEXAMINATION CERTIFICATE (8353rd)
United States Patent
Schwarze et al.

(10) Number: US 6,080,119 C1
(45) Certificate Issued: Jun. 28, 2011

(54) PROCESS AND DEVICE FOR GENERATING SHOCK WAVES FOR MEDICAL USES

(75) Inventors: Werner Schwarze, Kreuzlingen (CH); Walter Uebelacker, Buergeln (CH); Axel Voss, Egesdorf (DE)

(73) Assignee: Sanuwave, Inc., Marietta, GA (US)

Reexamination Request:
No. 90/011,035, Jul. 15, 2010

Reexamination Certificate for:
Patent No.: 6,080,119
Issued: Jun. 27, 2000
Appl. No.: 09/067,733
Filed: Apr. 28, 1998

(51) Int. Cl.
*A61B 17/22* (2006.01)

(52) U.S. Cl. .............. 601/4; 367/147; 606/127; 606/128

(58) Field of Classification Search .................. None
See application file for complete search history.

(56) References Cited

U.S. PATENT DOCUMENTS
5,251,614 A    10/1993    Cathignol et al.

FOREIGN PATENT DOCUMENTS
DE    1277716    9/1968
EP    0781447    7/1997

*Primary Examiner* — Jeffrey R. Jastrzab

(57) ABSTRACT

Acoustic shock waves for medical uses are generated by an electrical discharge between two electrodes, which are mounted in a liquid medium. A catalyst is added to the liquid medium in the area of the electrodes; this catalyst partially or completely catalytically converts the gas which forms upon application of the voltage to the electrodes back into its original state or partially or completely prevents the formation of the gas.

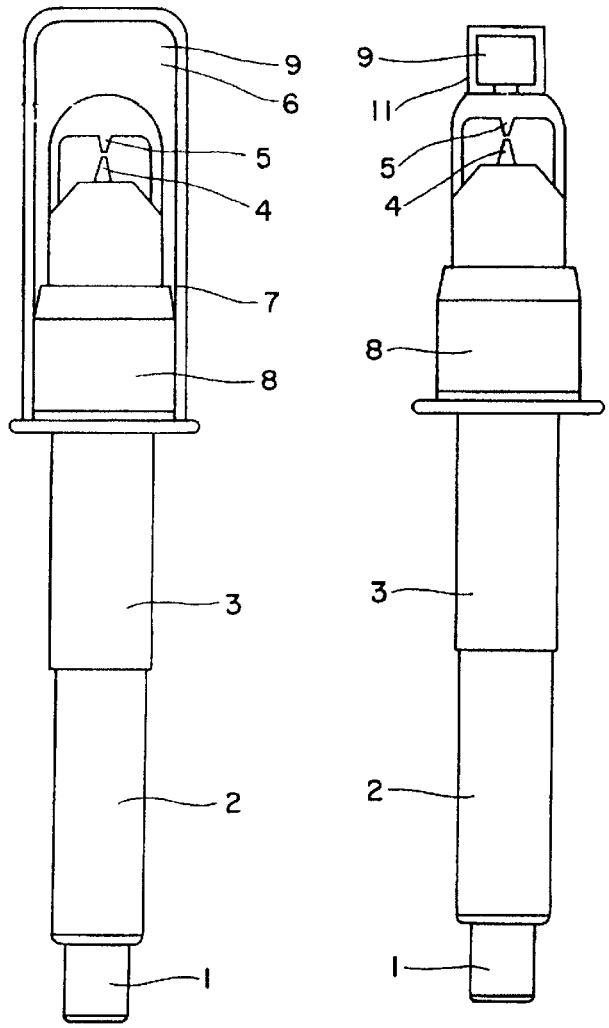

EX PARTE REEXAMINATION CERTIFICATE ISSUED UNDER 35 U.S.C. 307

Figure 1:
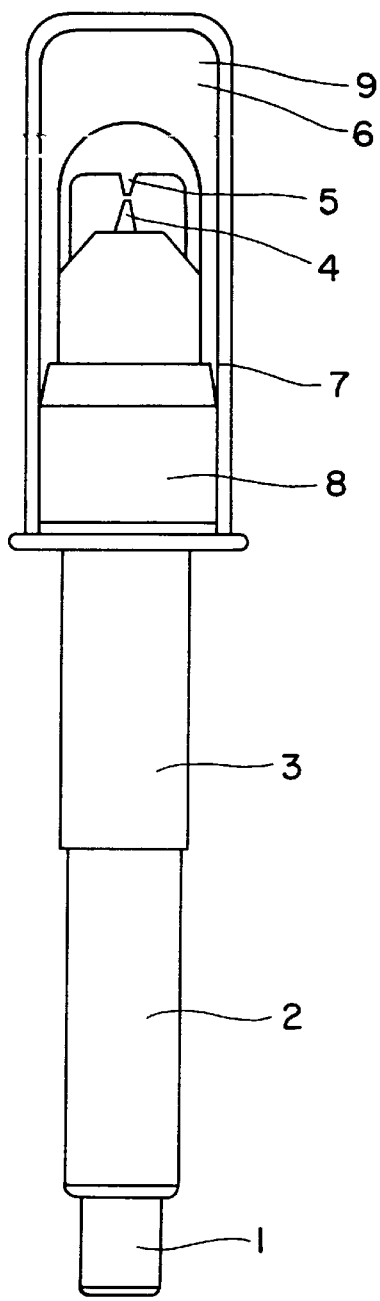
Figure 2:
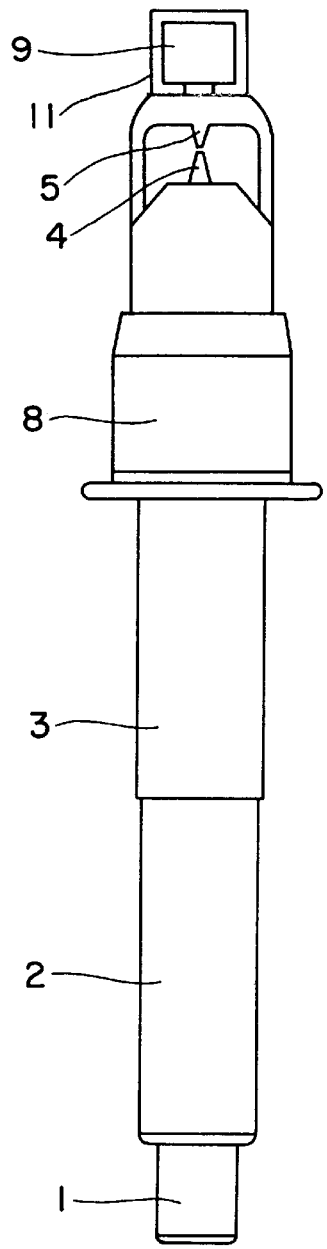

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 9 and 10 are cancelled.

Claims 1-4, 11 and 12 are determined to be patentable as amended.

Claims 5-8, dependent on an amended claim, are determined to be patentable.

1. In the process for generating shock waves for medical uses by application of a high electrical voltage to two electrodes mounted in a liquid medium, wherein the improvement comprises adding to said liquid medium at least in the area surrounding the electrodes an effective amount of a catalyst *providing a catalyst concentration of from 0.1 mg/mL to 4 mg/mL* to suppress electrolytic formation of gases due to application of said high voltage to said electrodes.

2. In the process for generating shock waves for medical uses by application of a high electrical voltage to two electrodes mounted in a liquid medium, wherein the improvement comprises adding to said liquid medium at least in the area surrounding the electrodes an affective amount of a catalyst *to provide a catalyst concentration of from 0.1 mg/mL to 4 mg/mL* to promote formation of said liquid medium by recombination of gases formed by application of said high voltage to said electrodes.

3. A process for suppressing formation and/or promoting recombination of gases formed during generation of shock waves *for medical uses* by application of a high electrical voltage to two electrodes mounted in a liquid medium, which process comprises adding to said liquid medium an effective amount of a catalyst *to provide a catalyst concentration of from 0.1 mg/mL to 4 mg/mL* to suppress formation and/or promote recombination of said gases.

4. A device for generating shock waves for medical uses by means of a high voltage electrical spark discharged comprising:
   (a) a pair of electrical spark discharge electrodes; and
   (b) a liquid medium containing an effective amount of a catalyst *providing a catalyst concentration of from 0.1 mg/mL to 4 mg/mL* to suppress formation and/or promote recombination of gases formed as a result of said high voltage electrical spark discharge.

11. A device for generating shock waves for medical uses by means of a high voltage electrical spark discharge comprising:
   (a) a pair of electrical spark discharge electrodes;
   (b) a liquid medium; and
   (c) a catalyst dispersed in said liquid medium in an effective amount *providing a catalyst concentration of from 0.1 mg/mL to 4 mg/mL* to suppress formation and/or promote recombination of gases formed as a result of said high voltage electrical spark discharge.

12. A device for producing shockwaves *for medical uses* by means of an electrical spark gap discharge comprising: a housing containing a liquid medium; a pair of closely-spaced discharge electrodes, an enclosure disposed about said electrodes in said housing; an electrically conductive liquid medium filling said enclosure, said electrically conductive liquid medium having an effective amount of a catalyst *providing a catalyst concentration of from 0.1 mg/mL to 4 mg/mL* to suppress formation and/or promote recombination of gases formed as a result of said high voltage electrical spark discharge.

\* \* \* \* \*